(12) United States Patent
Jones

(10) Patent No.: US 7,694,873 B1
(45) Date of Patent: Apr. 13, 2010

(54) INSTALLATION OF GERMICIDAL LIGHTS IN VENDING MACHINES

(76) Inventor: Taylor Wesley Jones, 2655 Creek Stone Cir., Maryville, TN (US) 37804

( * ) Notice: Subject to any disclaimer, the term of this patent is extended or adjusted under 35 U.S.C. 154(b) by 112 days.

(21) Appl. No.: 11/585,558

(22) Filed: Oct. 24, 2006

Related U.S. Application Data

(60) Provisional application No. 60/729,517, filed on Oct. 24, 2005.

(51) Int. Cl.
*A47G 29/14* (2006.01)
(52) U.S. Cl. .................. 232/27; 422/300; 422/24; 222/52; 379/452; 315/291
(58) Field of Classification Search ............. 210/105; 221/124; 232/27; 21/76, 75, 58; 422/300, 422/24; 222/52; 379/452
See application file for complete search history.

(56) References Cited

U.S. PATENT DOCUMENTS

| | | | | | |
|---|---|---|---|---|---|
| 2,148,143 | A | * | 2/1939 | Waitzman | 426/234 |
| 3,920,394 | A | * | 11/1975 | Marrapodi | 206/213.1 |
| 5,112,477 | A | * | 5/1992 | Hamlin | 210/85 |
| 5,441,179 | A | * | 8/1995 | Marsh | 222/190 |
| 5,487,877 | A | * | 1/1996 | Choi | 422/300 |
| 5,881,913 | A | * | 3/1999 | Boulter | 222/2 |
| 6,093,312 | A | * | 7/2000 | Boulter | 210/86 |
| 6,096,264 | A | * | 8/2000 | Peifer | 422/1 |
| 6,139,726 | A | * | 10/2000 | Greene | 210/94 |
| 6,301,359 | B1 | * | 10/2001 | Roberts | 379/452 |
| 6,365,113 | B1 | * | 4/2002 | Roberts | 422/186.3 |
| 6,458,331 | B1 | * | 10/2002 | Roberts | 422/186.3 |
| 6,490,351 | B1 | * | 12/2002 | Roberts | 379/452 |
| 7,038,398 | B1 | * | 5/2006 | Lys et al. | 315/291 |
| 7,067,089 | B2 | * | 6/2006 | Wen | 422/292 |
| 7,285,254 | B2 | * | 10/2007 | Lin et al. | 422/300 |
| 7,348,572 | B2 | * | 3/2008 | Shin | 250/455.11 |
| 2003/0085266 | A1 | * | 5/2003 | Simon | 232/27 |
| 2004/0108327 | A1 | * | 6/2004 | Baack et al. | 221/124 |

* cited by examiner

*Primary Examiner*—Gene O. Crawford
*Assistant Examiner*—Rakesh Kumar
(74) *Attorney, Agent, or Firm*—Luedeka, Neely & Graham, PC

(57) ABSTRACT

A vending machine for dispensing products includes a germicidal light for disinfecting a product dispensed by the vending machine. The germicidal light is positioned adjacent an exit chute of the vending machine such that it exposes the product to a sterilizing frequency of light when the product is dispensed. Alternatively, the products may be intermittently exposed to the sterilizing light while the products are on display in accordance with a predetermined exposure schedule. The invention is particularly effective when it is used in connection with a canned drink machine.

2 Claims, 5 Drawing Sheets

INSTALLATION OF GERMICIDAL LIGHTS IN VENDING MACHINES

CROSS-REFERENCES TO RELATED APPLICATIONS

This application is a Non-Provisional Utility application which claims benefit of U.S. Patent Application Ser. No. 60/729,517 filed Oct. 24, 2005, entitled "INSTALLATION OF GERMICIDAL LIGHTS IN VENDING MACHINES" which is hereby incorporated by reference.

STATEMENT REGARDING FEDERALLY SPONSORED RESEARCH OR DEVELOPMENT

Not Applicable

REFERENCE TO SEQUENCE LISTING OR COMPUTER PROGRAM LISTING APPENDIX

Not Applicable

FIELD OF THE INVENTION

The present invention is directed generally toward a sanitary vending machine. More particularly, an embodiment of the present invention is directed toward a vending machine that uses a germicidal light to sterilize products dispensed from the machine.

BACKGROUND OF THE INVENTION

Millions of American eat and drink from vending machines on a daily basis. Unfortunately, many of the products, such as drinks in aluminum cans, are consumed directly out of the packaging. As the person's lips and mouth come into contact with the exterior of the package or can, they are exposed to any bacteria or germs that may be on the can. These germs can come from the hands of individuals that came in to contact with the can or product, the internal portions of the machine, storage facilities or simply from the air surrounding the products and the vending machine. Also, after the Sep. 11, 2001 attacks, and the wide attention to anthrax being passed in the mail and on packages, more concern is being directed toward preventing intentional contamination of food items. Thus, people are now more likely than ever to question whether products purchased from vending machines are safe and sanitary.

BRIEF SUMMARY OF THE INVENTION

An embodiment of the present invention is directed toward a vending machine for dispensing products. The vending machine includes a germicidal light for disinfecting a product dispensed by the vending machine. The germicidal light exposes the product to a sterilizing frequency of light when the product is dispensed. The products may also be exposed to the germicidal light in accordance with an exposure schedule. Preferably, the vending machine dispenses drinks in cans and the germicidal light includes, at a minimum, two 25 watt fluorescent bulbs.

Another embodiment of the present invention is directed toward a machine for dispensing a product. The machine includes a light source for exposing the product to a sterilizing frequency light wave such that an exterior surface of the product is sanitized prior to the product being dispensed. The light source is positioned along an exit chute of the vending machine such that the product is exposed to the sterilizing light when it is dispensed. The light source may also be positioned adjacent a product display area of the vending machine such that the product is exposed to the sterilizing light for a predetermined exposure period while it is displayed.

Yet another embodiment of the present invention is directed toward a method of dispensing a product from a vending machine. The vending machine includes a germicidal light source positioned along an exit chute of the vending machine. In accordance with the method, the product is exposed to a sterilizing frequency light wave prior to the product being dispensed from the vending machine. The product is exposed to the sterilizing light for a predetermined exposure period prior to the product being dispensed.

DETAILED DESCRIPTION OF THE INVENTION

The present invention addresses the aforementioned problems of the prior art by placing a sterilizing, germicidal light in vending machines that sterilizes or substantially reduces bacteria present on the exterior packaging of the product being dispensed. The sterilizing light is placed on both sides of the exit chute of the vending machine where the cans or products are expelled from the machine. When money is placed in the machine to purchase a canned drink, the light is activated. As the drink comes down the exit chute, the lights placed on each side of the chute illuminate to expose the can to the sterilizing light. The light does not penetrate the can but, kills substantially all of the bacteria on the surface of the can in seconds. The wattage of the bulbs will determine how long the light will need to be illuminated. A stronger wattage bulb of at least 50 watts can kill bacteria in seconds while a lower wattage bulb requires a longer period of light exposure. Thus, when a germicidal light is installed in a vending machine in accordance with an embodiment of the present invention, it can safely kill many strains of bacteria and other organisms, including the vegetative form of anthrax that may be present on the product being dispensed. Therefore, the present invention provides reassurance to consumers that they are purchasing safe and sanitary products when using vending machines.

Figure 1:
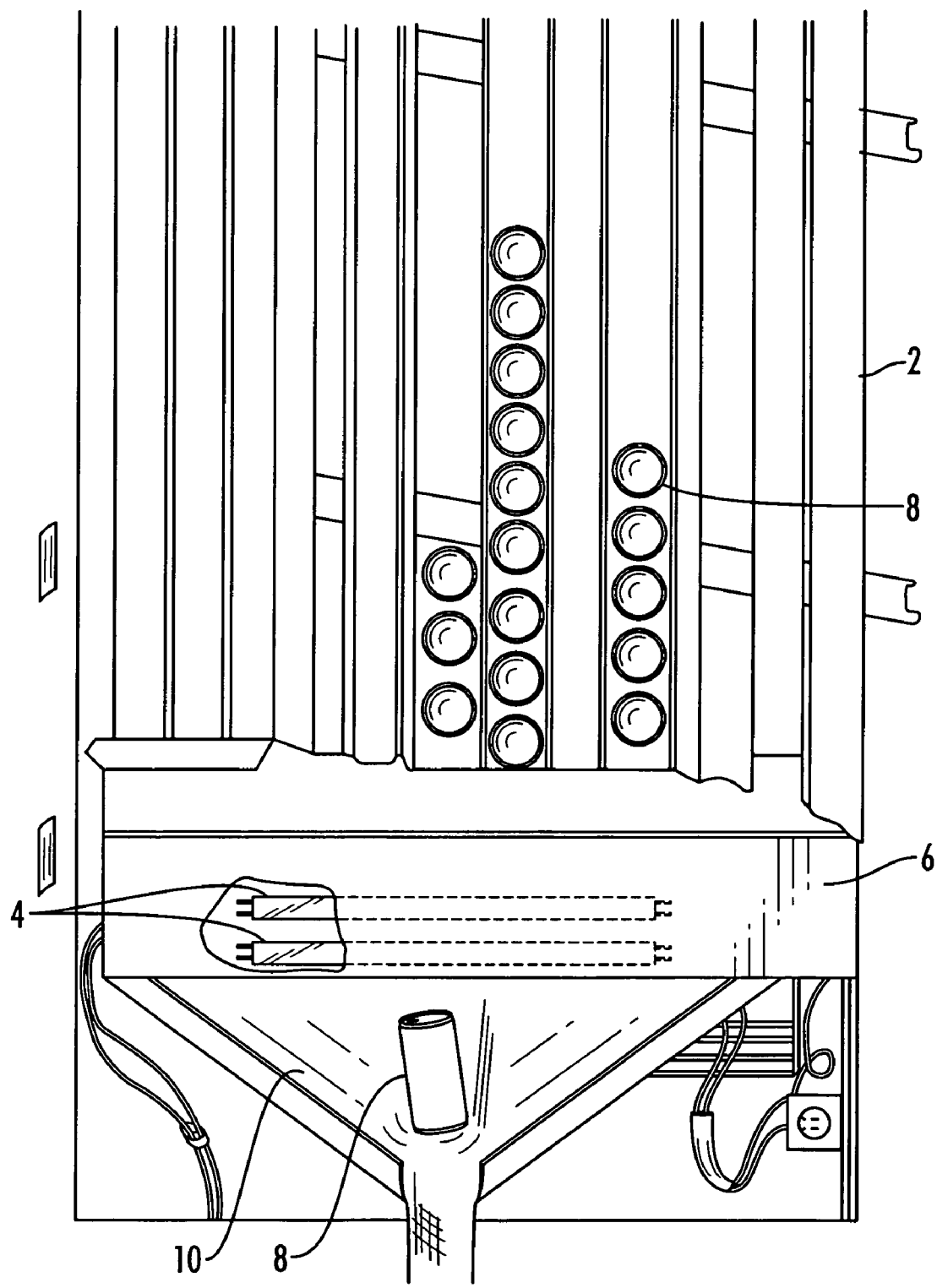
FIG. 1 is an illustration of a drink vending machine constructed in accordance with an embodiment of the present invention.

Referring now to FIG. 1, an illustration of a drink vending machine 2 constructed in accordance with an embodiment of the present invention is shown. The face of the vending machine 2 has been removed in the illustration so that the internal drink can dispensing mechanisms can be seen. In a working embodiment, the front of the machine 2 will be covered in a manner similar to that of a typical vending machine with advertising printed thereon. A germicidal light 4, such as an ultraviolet frequency sterilization light, is positioned in the vending machine 2 so that a drink can 8 being dispensed from the vending machine is exposed to light from the germicidal light 4 as it exits the vending machine 2. In FIG. 1, the germicidal light 4 is positioned under the shield protector 6 of the vending machine 2. However, the light 4 can positioned anywhere the dispensed product will come into contact with the sterilizing light as discussed in more detail herein. A standard drink vending machine 2 measures 37" width; 80" length, and 26" deep. The piece of steel on which the bulb is positioned measures 32" in length and 4¾" in width. The sterilizing light 4 preferably measures 18" long and includes (2) 25-watt sterilizing bulbs.

When the can 8 is dispensed through the exit chute 10 of the vending machine 2, the can is exposed to the light 4 such that the exterior of the can 8 is sterilized, or at least sanitized, prior to being dispensed to the purchaser. The degree of sterilization obtained by the system depends upon the time which the product 8 is exposed to light 4, the intensity of the light 4 and the number of lights positioned along the exit path 10 of the product. Thus, the exit path 10 may be configured to prolong the product's 8 exposure to the light 4 as it exits the machine 2 and thus, the degree of sterilization provided by the system. In addition, the product 8 may be made to be held and rotated in front of the light 4, or additional lights 4 positioned around the periphery of the exit path 10, to insure that all surfaces of the product 8 are exposed to the light 4 as the product 8 is dispensed. Lights 4 having different frequencies of operation will also produce varying degrees of sterilization as is known in the art.

Figure 2:
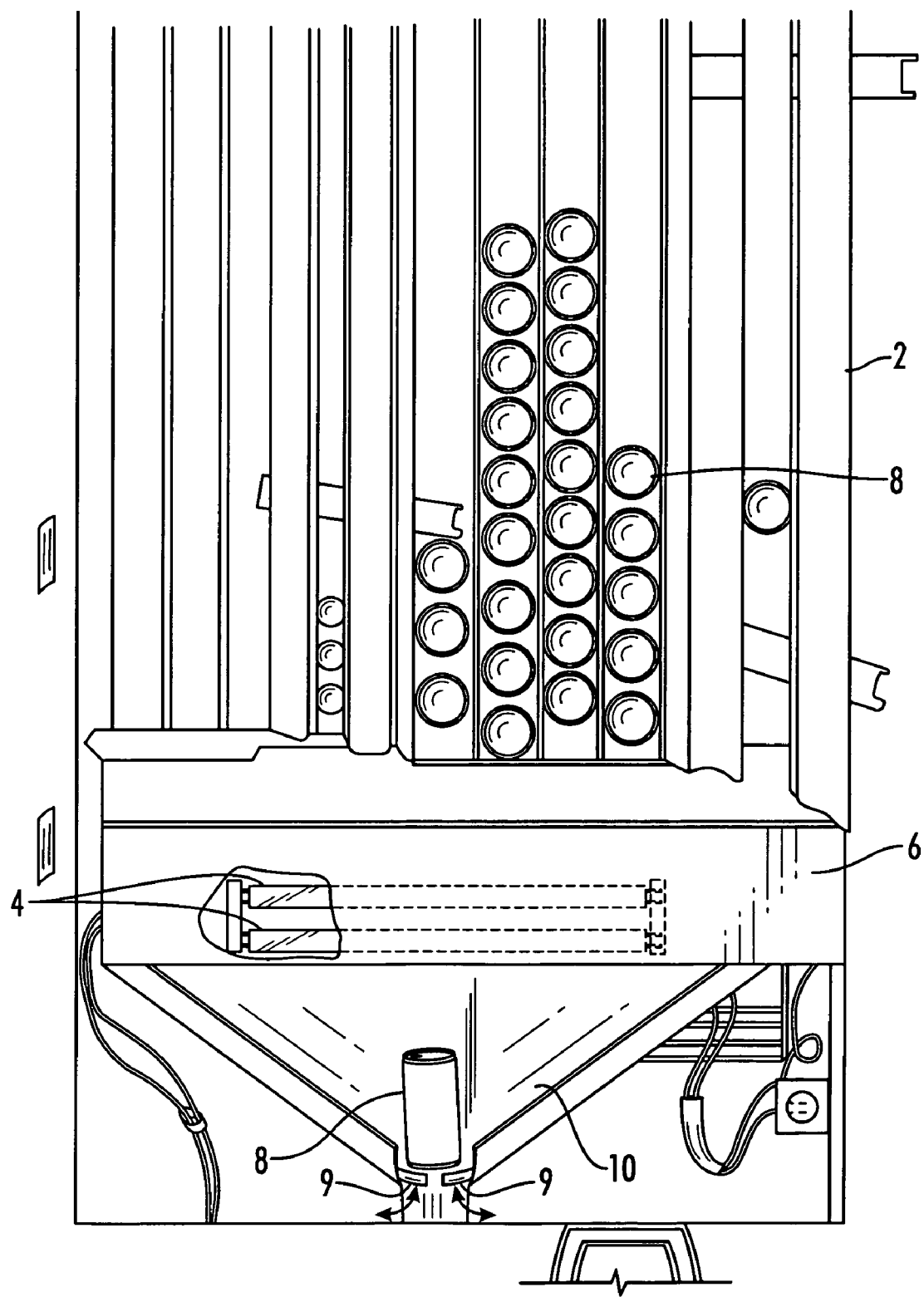
FIG. 2 is an illustration of a drink vending machine constructed in accordance with an alternative embodiment of the present invention.

Referring now to FIG. 2, an illustration of a drink vending machine 2 constructed in accordance with an alternative embodiment of the present invention is shown. The embodiment of FIG. 2 functions in a similar manner to that of FIG. 1. Thus, when drink can 8 is dispensed through the exit chute 10 of vending machine 2, the can is exposed to light 4. However, in the embodiment of FIG. 2, the product or can 8 is held and/or rotated by levers 9 in a stationary position while exposed to the germicidal light 4. This insures complete coverage of the dispensed product 8 and allows the product 8 to be exposed to the light 4 for a predetermined exposure period.

Figure 3:
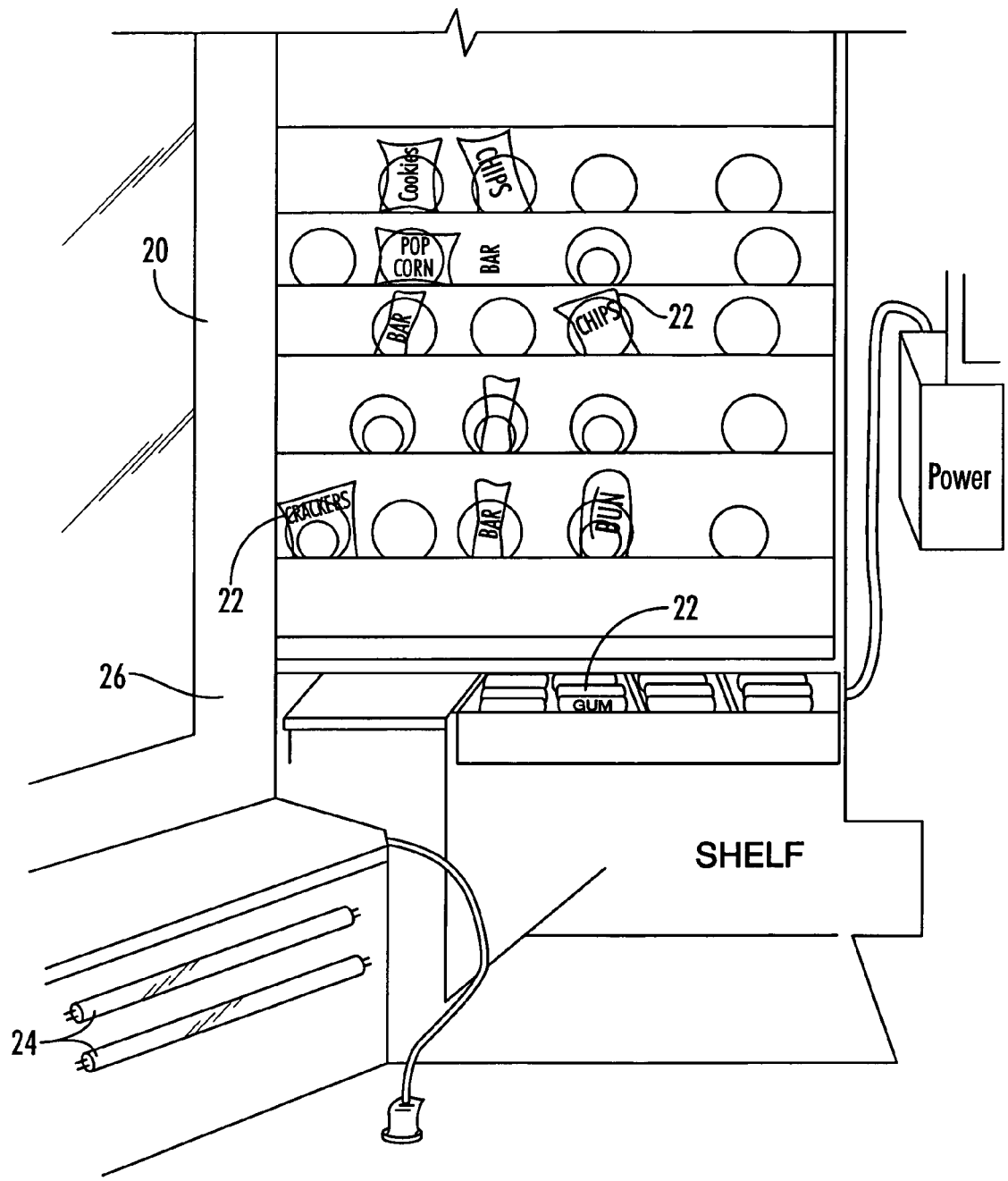
FIG. 3 is an illustration of a product vending machine constructed in accordance with an embodiment of the present invention.

Referring now to FIG. 3, an illustration of a product vending machine 20 constructed in accordance with an embodiment of the present invention is shown. The vending machine 20 dispenses packaged products 22 such as chips, gum and candy bars. When a product 22 is dispensed, it is exposed to a germicidal light 24 that is positioned on the interior of the front door 26 of the vending machine 20. The germicidal light 24 kills at least a portion of any bacteria residing on the package of the product 22 such that the risk of the product 22, or the individual consuming the product 22, being contaminated by bacteria is decreased. In the embodiment shown, two 25 watt fluorescent ultraviolet bulbs 24 are used for sterilization. A timing mechanism can be used to prevent the dispensing door of the vending machine 20 from opening such that the purchaser can not remove the product 22 from the machine 20 until the product has been sterilized for a predetermined exposure period. This insures that the package is exposed to the light for an amount of time that is sufficient to kill any bacteria present on the product package before the product 22 is removed.

Figure 4:
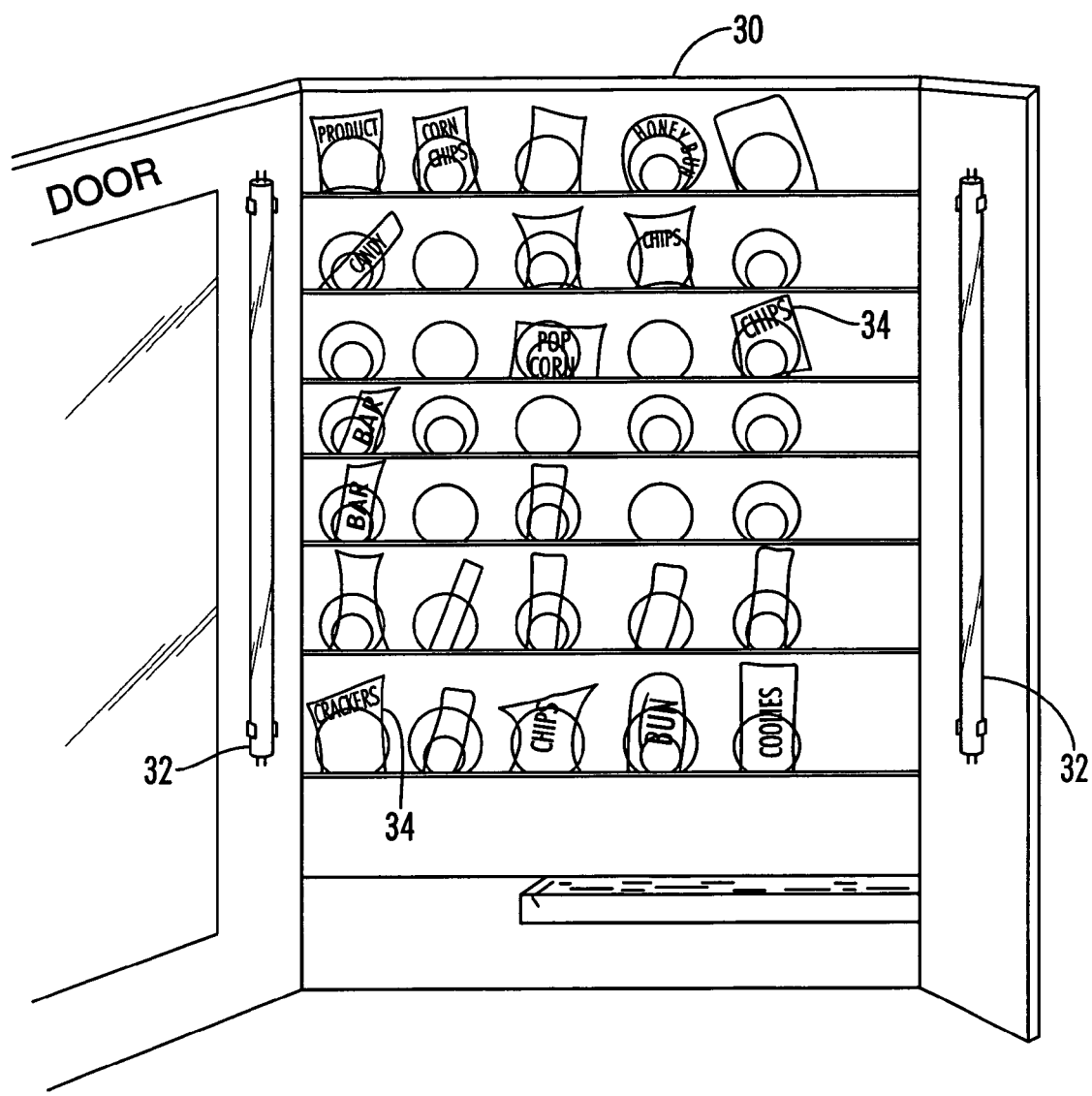
FIG. 4 is an illustration of a product vending machine constructed in accordance with an alternative embodiment of the present invention.

Referring now to FIG. 4, an illustration of a product vending machine 30 constructed in accordance with an alternative embodiment of the present invention. In the embodiment of FIG. 4, the germicidal lights 32 are positioned in the vending machine 30 such that the products 34 are exposed to the germicidal light's output while they are on display. The germicidal lights 32 may be permanently on or intermittently turned on for an exposure period such as for one minute during every hour. In addition, germicidal lights can also be positioned near the dispensing door of the vending machine as described above with respect to FIG. 4 to further insure that the product's packaging is not contaminated with disease causing organisms.

Figure 5:
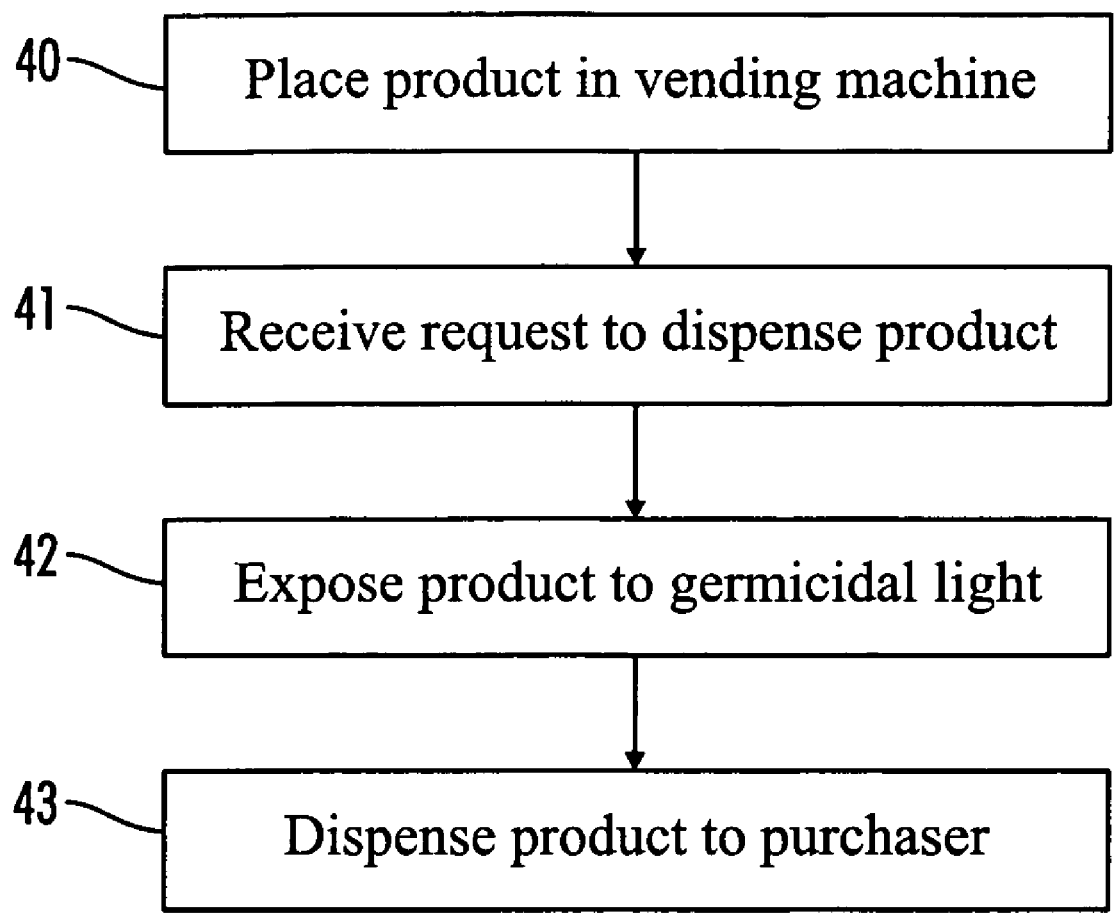
FIG. 5 is a flow chart of a method of sterilizing a product dispensed from a vending machine in accordance with an embodiment of the present invention.

Referring now to FIG. 5, a flow chart of a method of dispensing a product from a vending machine is shown. The method commences in step 40 with the positioning of the product to be sold in the vending machine. In step 41, a request to dispense a product is received from the vending machine's controller. Typically, this would be generated in response to a customer paying for and selecting a product. In response to the dispensing request, the product being dispensed is exposed to a germicidal light in step 42 to kill any bacteria present on the device's packaging. Once the product has been sterilized, it is dispensed to the purchaser in step 43.

Although there have been described particular embodiments of the present invention of a new and useful VENDING MACHINE WITH GERMICIDAL LIGHT herein, it is not intended that such references be construed as limitations upon the scope of this invention except as set forth in the following claims.

What is claimed is:

1. A method of dispensing a packaged food product from a vending machine, said method comprising:
    providing a vending machine having a food product storage area and a food product dispensing area;
    locating a plurality of packaged food products within the food product storage area;
    dispensing the food products from the vending machine via the dispensing area;
    exposing said packaged food product to a sterilizing frequency light wave located within the dispensing area of the vending machine for disinfecting a packaged food product dispensed by said vending machine to a consumer, the light being activated when the product is being dispensed and located within the dispensing area.

2. The method of claim 1 wherein the step of exposing the packaged food product to a sterilizing frequency light comprises exposing the packaged food product to light from a germicidal light source positioned along an exit chute of said vending machine.

* * * * *